United States Patent [19]
Vonesh et al.

[11] Patent Number: 5,152,293
[45] Date of Patent: Oct. 6, 1992

[54] FINGER-MOUNTED INTRAOPERATIVE IMAGING DEVICE

[75] Inventors: Michael J. Vonesh, Northbrook; Fouad H. Khasho, Niles, both of Ill.

[73] Assignee: Northwestern University, Evanston, Ill.

[21] Appl. No.: 724,201

[22] Filed: Jul. 1, 1991

[51] Int. Cl.$^5$ .............................................. A61B 5/02
[52] U.S. Cl. ........................... 128/662.03; 128/662.04; 128/691; 128/381
[58] Field of Search ...................... 128/660.10, 661.09, 128/662.03, 662.04, 672, 690, 691, 381, 800

[56] References Cited

U.S. PATENT DOCUMENTS

| | | | |
|---|---|---|---|
| 4,744,368 | 5/1988 | Young et al. | 128/662.04 |
| 4,794,931 | 1/1989 | Yock | 128/660.03 |
| 4,807,639 | 2/1989 | Shimizu et al. | 128/690 |
| 4,926,875 | 5/1990 | Rabinovitz et al. | 128/691 |
| 4,986,276 | 1/1991 | Wright | 128/662.04 |
| 5,088,500 | 2/1992 | Wedel et al. | 128/662.06 |

OTHER PUBLICATIONS

Likoff et al, Epicardial Mapping of Segmental Myocardial Function . . . , Circulation, vol. 66, No. 5, pp. 1050–1058 (Nov. 1982).

*Primary Examiner*—Francis Jaworski
*Assistant Examiner*—George Manuel
*Attorney, Agent, or Firm*—Tilton Fallon Lungmus

[57] ABSTRACT

A small, disposable device for use in intraoperative diagnostic imaging in the form of a finger-mounted probe having an elongated chamber along its longitudinal midline for removably receiving the distal end of an ultrasonic imaging catheter equipped with an ultrasound generator having an imaging plane normal to the probe's longitudinal midline. The probe includes a body formed of relatively rigid non-echogenic material with an upper surface of concave cross-sectional contour shaped and dimensioned to receive the underside of a user's finger and also includes an integral retention band that bridges the body and extends over the tip portion of a user's finger when the probe is worn. A Doppler generator/detector may be mounted in the distal end wall of the probe for directing, detecting, and transmitting signals representative of blood flow velocity through a vessel contacted by the smooth undersurface of the probe along the imaging plane of the ultrasonic imaging catheter extending into the probe's chamber. In one embodiment, a tubular hydrogel liner is disposed within the chamber, such liner having an axial passage for freely receiving the distal end of an imaging catheter when the hydrogel is unhydrated and for firmly engaging and retaining the distal end, and maintaining an acoustic couple, when the hydrogel is hydrated.

24 Claims, 2 Drawing Sheets

FINGER-MOUNTED INTRAOPERATIVE IMAGING DEVICE

BACKGROUND AND SUMMARY

Intraoperative diagnostic procedures are considered of fundamental importance in surgery. They may augment the findings of previous exams and often yield information not procurable by other means. Surgical management of the patient can thus be improved through such procedures by providing the information necessary to plan, modify, or evaluate a surgical intervention.

Past methods and devices for acquiring intraoperative vascular data have a number of shortcomings. Relatively large hand-held ultrasonic imaging probes have been available but their hand-held design and overall dimensions make them difficult to maneuver within the thoracic cavity. Their size and design therefore limits the extent of examination that can be performed. Also, such hand-held imagers often utilize a mechanical means for sector scanning, resulting in mechanical vibrations of the instrument that may have the potential of embolizing intravascular plaque and thrombi in addition to the possibility of damaging suture integrity. In general, such probes are expensive, non-disposable, and provide little tactile feedback to the operator.

Similarly, present methods of intraoperative blood flow measurement possess their share of disadvantages. Intraoperative flow velocity estimation techniques are limited in their range of applications and the instruments are difficult to position properly, require intensive operator interaction, and in many situations yield inaccurate results.

Accordingly, a main aspect of this invention lies in providing a relatively small, disposable, finger-mounted device for facilitating the intraoperative evaluation of vascular morphology and blood flow characteristics. The finger-mounted probe is combinable with a conventional, miniaturized, ultrasound imaging catheter and, in a preferred embodiment, provides both two-dimensional ultrasonic imaging and Doppler blood flow indications. Using the device, a surgeon may collect comprehensive anatomic and hemodynamic information of selected vascular segments simply by touching the surface of interest with his/her fingertip. In such a manner, diagnostic vascular information may be acquired from virtually any site in the surgical field that the surgeon's fingers can reach.

The probe, being separable from the imaging catheter, may be fabricated inexpensively enough for one-time use. Because of its construction, size, and finger attachment, it provides tactile feedback throughout an examination procedure. Although the probe may be used with a conventional intravascular imaging catheter, such catheter is used in an extravascular, not intravascular manner.

Briefly, the probe includes an elongated, channel-shaped body formed of relatively rigid, non-echogenic material that is substantially transparent to ultrasonic energy. The body has a smoothly-curved lower surface and an upper surface of concave cross sectional contour dimensioned to receive the underside of a user's finger, preferably the index finger. An integral band bridges the body and serves as retaining means for holding the probe on a surgeon's finger. An elongated chamber extends inwardly from the body's proximal end along the longitudinal midline thereof and removably receives the distal segment of an ultrasound 2-D-echo mode imaging catheter having an ultrasonic transducer with an imaging plane normal to such longitudinal midline for emitting ultrasonic pulses and for receiving and transmitting ultrasonic reflections. Ideally, the imaging plane is aligned with the retention band that extends over the tip of a user's finger and provides a visual aid to the user in positioning the probe in relation to the vascular area of evaluation. A Doppler generator/detector is preferably mounted in the distal end of the body and is directed towards the imaging plane of the ultrasound catheter for directing, detecting, and transmitting signals representative of blood flow velocity through a vessel contacted by the smooth undersurface of the probe.

Aqueous fluid such as sterile saline is introduced into the chamber to surround the imaging catheter and provide an acoustic couple between the catheter and the probe. Irrigation ports leading from the chamber to the underside of the probe, and also from the chamber to the probe's upper surface, allow small amounts of the fluid to escape from the chamber and provide an acoustic couple between the user's finger, the probe, and the surface under investigation.

In one embodiment, the catheter-receiving chamber of the probe is lined with a tubular hydrogel liner. In its unhydrated state the liner defines a passage considerably larger in cross section than that of a catheter to be received therein, thereby facilitating catheter insertion when the parts are being assembled for use. Hydration of the hydrogel liner by sterile saline introduced into the chamber causes a swelling of the liner which in turn fills the voids, eliminates air pockets, secures the catheter in place, and provides an acoustic couple between the catheter and the probe.

Other features, advantages, and objects will be apparent from the specification and drawings.

DRAWINGS

DETAILED DESCRIPTION OF PREFERRED EMBODIMENTS

Figure 1:
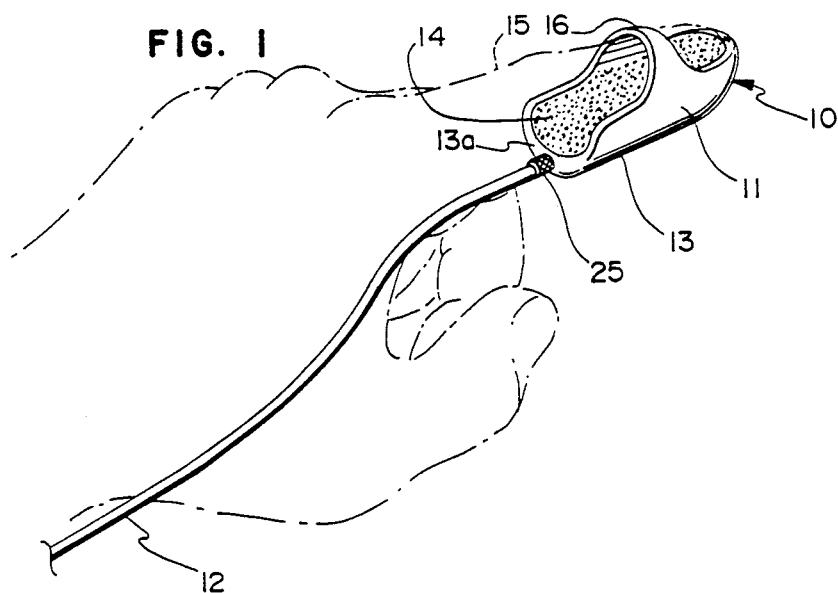
FIG. 1 is a perspective view of the device embodying the present invention such device being shown as it would be worn in use.

Referring to FIG. 1, the numeral 10 generally designates a finger-mounted intraoperative imaging device comprising a finger probe or receptacle 11 and an ultrasound imaging catheter 12. The probe includes an elongated body 13 having proximal and distal ends 13a and 13b, respectively. The body is channel shaped with an upper surface 14 of concave cross-sectional curvature dimensioned to receive the lower portion of a user's finger distal to the second knuckle (i.e., the knuckle joint between the second and third phlanges), preferably that of the index finger 15 as depicted in phantom in FIGS. 1 and 2. Such upper surface may be stippled or otherwise textured to provide a non-slip surface for finger contact. At its distal end, upper surface 14 curves upwardly to conform with the contour of the user's fingertip.

The probe also includes an integral band 16 which functions as retaining means for holding the probe on the finger. The band bridges the body 13 and is positioned to arch over the tip of the finger beyond its distal joint.

Figure 3:
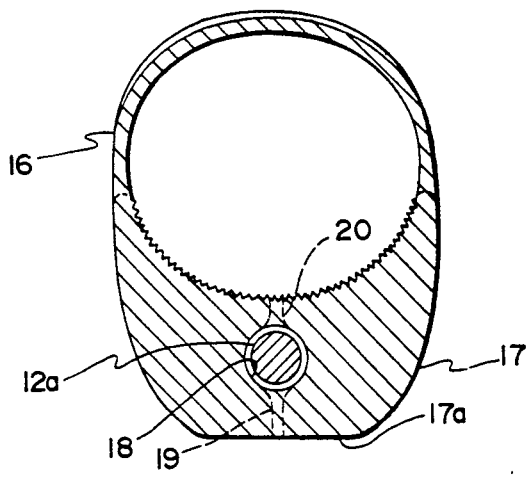
FIG. 3 is an enlarged cross sectional view taken along line 3—3 of FIG. 2.
Figure 4:
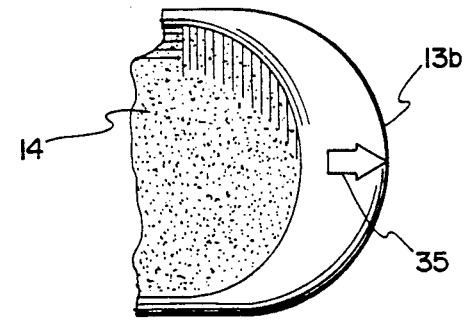
FIG. 4 is a fragmentary top plan view of the distal end of the probe.

The outer surface 17 of the probe is smoothly rounded or curved as depicted in the drawings although, if desired, the undersurface 17a may be flattened somewhat as shown in FIG. 3 to promote more even or uniform contact with a surface against which the probe is urged.

Figure 2:
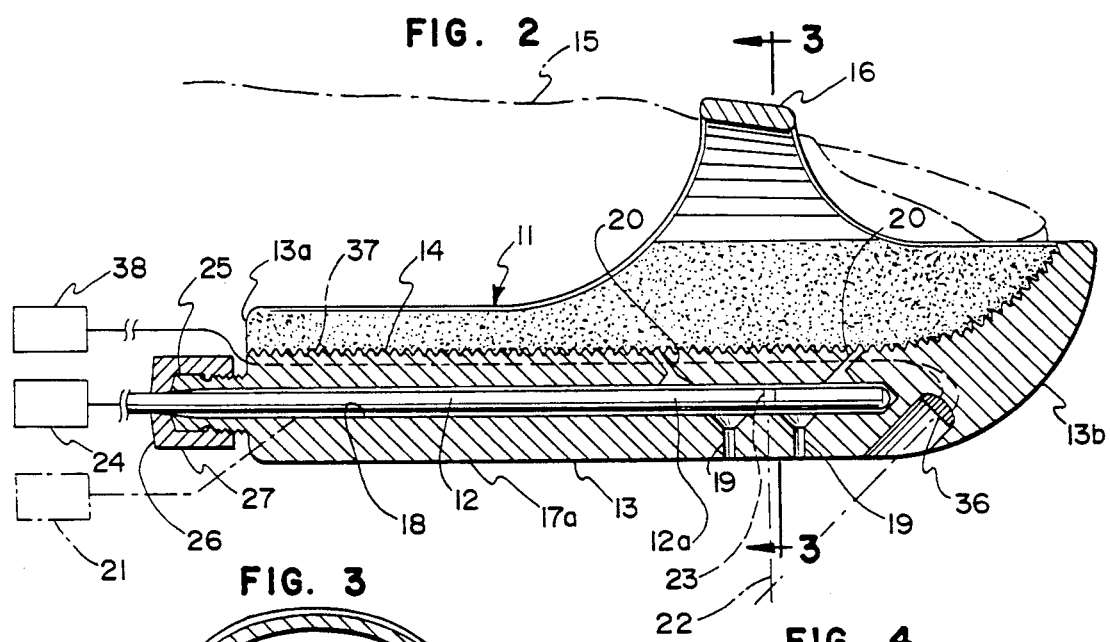
FIG. 2 is an enlarged longitudinal sectional view of the device.

An elongated cylindrical chamber 18 extends into the body 13 from its proximal end 13a and terminates near the body's distal end 13b. As shown in FIGS. 2 and 3, an ultrasound imaging catheter 12 has its distal segment 12a received within chamber 18. The diameter of the chamber is larger than the outside diameter of the catheter to define a space through which sterile saline or other aqueous fluid may be introduced to provide an acoustic couple between the probe and the catheter. In addition, the body of the probe is advantageously provided with irrigation ports 19 and 20 which extend between the chamber and the undersurface 17a and upper surface 14, respectively. The escape of fluid from the chamber through ports 19 and 20 provides an acoustic couple between the probe and the surface it contacts, and between the probe and the user's finger 15. Any suitable reservoir and pumping means 21 may be placed in communication with chamber 18 for supplying the aqueous fluid to that chamber (FIG. 2). Alternatively, the catheter 12 may itself be provided with a passage leading to its distal end through which fluid may be supplied to chamber 18 and ports 19, 20.

The miniaturized catheter may be a conventional ultrasound imaging catheter such as the type marketed for intravascular use by Cardiovascular Imaging Systems Incorporated, Sunnyvale, Calif. and shown and described in U.S. Pat. No. 4,794,931. Such a catheter includes an ultrasonic transducer and rotating mirror enclosed within a transparent acoustic housing at the distal segment of the catheter. The catheter assembly houses a drive cable which is used to rotate the mirror, and the lumen of the catheter may be flushed with sterile saline to expel air prior to use and to provide an acoustic medium for ultrasound imaging. Alternatively, the ultrasound imaging catheter may be of a type having a multiplicity of crystals arranged in an annular array, or of the type having a multiplicity of crystals arranged in a phased array typically found in a transesophageal echocardiographic probe, instead of a single crystal associated with a mirror rotated about a drive cable. In any case, catheter 12 takes the form of a standard imaging catheter capable of operating in a 2-D-echo mode to provide a transverse imaging plane 22. Such imaging plane is therefore normal to the longitudinal midline of the probe's body 13 along which chamber 18 extends. In FIG. 2, the ultrasound generator or transducer is indicated at 23 and is generally aligned with the retention band 16. Consequently, when the imaging catheter has its distal segment fully inserted into the chamber 18 as shown, the ultrasound transducer 23 will directly underlie band 16 with the latter then serving as a visual and tactile indicator of the imaging plane. If desired, a conventional accoustic lens may be incorporated in the body 13 beneath band 16 and the imaging catheter 12 to focus the energy directed along the imaging plane.

It is important that the ultrasound imaging catheter 12 generate high-frequency ultrasound energy to formulate high resolution planar images. Specifically, the transducer should be capable of operating at a frequency range of 5 to 50 megahertz (MHz) to provide images of sufficient resolution to characterize all pertinent vascular structures. The compromise made to acquire such high resolution images is a restriction in the penetration depth of ultrasound energy to less than one centimeter; however, such a limitation is not a handicap because most of the vessels to be evaluated lie on the epicardium or are exposed during surgical intervention.

As disclosed in U.S. Pat. No. 4,794,931, high voltage pulses are supplied to the transducer 23 to produce ultrasonic waves which emanate therefrom into the surrounding tissue structure. Portions of the ultrasonic energy wave are reflected by the tissue structure back to the transducer with the transducer then acting as a receiver. The ultrasonic vibrations are converted into electrical signals and transmitted back to a receiver, amplifier, and display system schematically represented in FIG. 2 and designated by numeral 24. For further details of the ultrasound imaging system and its operation, reference may be had to the disclosure of the aforementioned patent. Since such systems are well known and commercially available, further discussion of the details thereof is believed unnecessary herein.

Mounting means are provided for releasably securing the distal end of the ultrasound imaging catheter in its operative position in chamber 18. In the embodiment illustrated in the drawings, the mounting means includes a threaded tubular collet 25 which may be formed integrally with probe 11 and which protrudes from the proximal end 13a of body 13. The catheter extends through the lumen of the collet which communicates directly with chamber 18. At its free end, the collet is provided with a plurality of jaws 26 with sloping end surfaces engaged by a nut 27 so that when the nut is tightened (as shown), the jaws are urged into tight frictional engagement with the outer surface of the catheter.

A Doppler transducer 36 is located along the underside of the probe 11 and is oriented so that its crystal faces towards imaging plane 22 and in a direction along, or at an angle to (preferably, at an angle of 45 degrees), the flow of blood through a vessel contacted by the probe. Leads 37 connect the transducer to suitable instrumentation 38 for generating ultrasonic pulses and for detecting the echoes and determining flow velocity as represented by the Doppler shift. Such instrumention is well known and commercially available, and has therefore been depicted only schematically in FIG. 2. Doppler transducers and instrumentation from various sources may be used effectively in connection with the embodiment of the invention, reference being had to the blood-flow measuring Dopplers marketed by Titronics Medical Instruments, Iowa City, Iowa, in that regard.

If desired, the distal end of the probe may be provided with a suitable visual indicator 35 to assist a surgeon in properly orienting the device. As previously stated, the imaging plane scans the tissue lying directly beneath and parallel to the retention band 16. The indicator 35 is directed perpendicular to the imaging plane and may be also used as a guide in the placement of the probe. Using these geometrical cues, a surgeon may align the transducers about any desired orientation. Such method of examination is natural, uncumbersome, and provides continual tactile feedback throughout the examination procedure.

When placed over the index finger, and with the imaging catheter 12 in place, the device enables a surgeon simultaneously to obtain ultrasonic images of vascular structures lying beneath his/her fingertip and blood flow velocities through such vascular structures at the imaging plane. By maintaining physical contact between the probe and the surface of interest, anatomic and hemodynamic data may be acquired to a depth of about one centimeter. Moving the finger probe and establishing an acoustic couple allows diagnostic data collection from virtually anywhere within the surgical field.

The probe may be constructed from any biocompatible, non-echogenic plastic that is relatively rigid and substantially transparent to ultrasonic energy. Methyl methacrylate or polycarbonate resins are believed particularly suitable, but other materials having similar properties may be used. High volume commercial manufacture may be accomplished through standard pressurized injection molding techniques, and sterilization may be achieved by ethylene oxide gasing following fabrication and packaging. The probe, which is separable from the catheter following use of the device, is therefore a relatively inexpensive, disposable item that may be discarded after a single use.

Referring to the embodiment of FIGS. 5-8, probe 111 is similar to the probe 11 already described except for the inclusion of liner 40 in elongated chamber 118. Thus, probe 111 may be equipped with an ultrasonic Doppler transducer and with irrigation ports 20 in the manner previously disclosed but those features have been omitted from FIGS. 5-8 for simplicity and clarity of illustration.

Chamber 118 is lined with a tubular liner 40 composed of a hydrogel such as polyhydroxyethyl methacrylate, although other hydrogels having similar properties are commercially available and may be used. In unhydrated or dehydrated condition, such a hydrogel is a rigid acrylic polymer capable of changing into an elastic gel when exposed to an aqueous solution. Depending on fabrication techniques, up to 90 percent of the hydrogel may be composed of water when the material is in hydrated condition.

Figure 5:
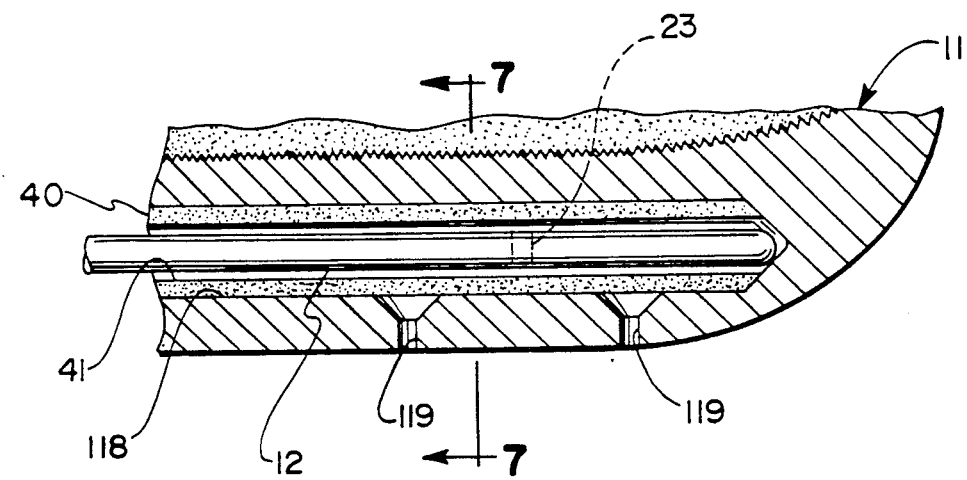
FIG. 5 is a fragmentary longitudinal sectional view depicting an alternate embodiment of the invention, such embodiment having an unhydrated hydrogel liner within the chamber of the probe.
Figure 6:
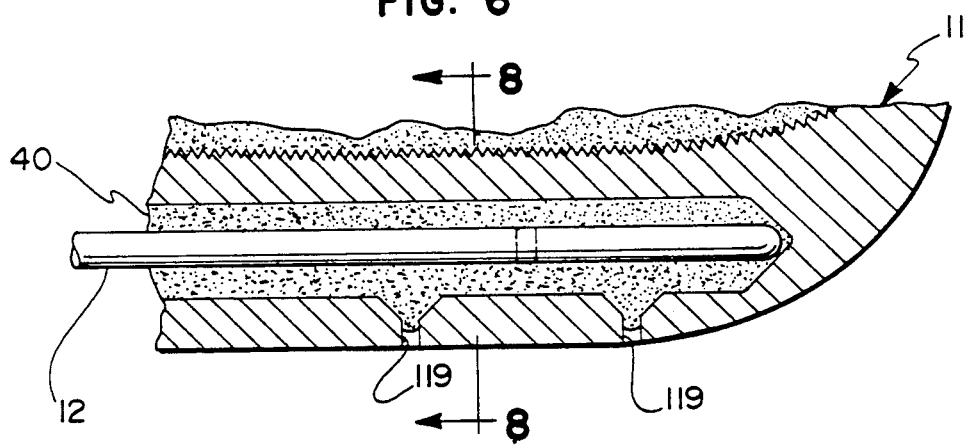
FIG. 6 is a longitudinal sectional view similar to FIG. 5 but showing the liner in hydrated condition.
Figure 7:
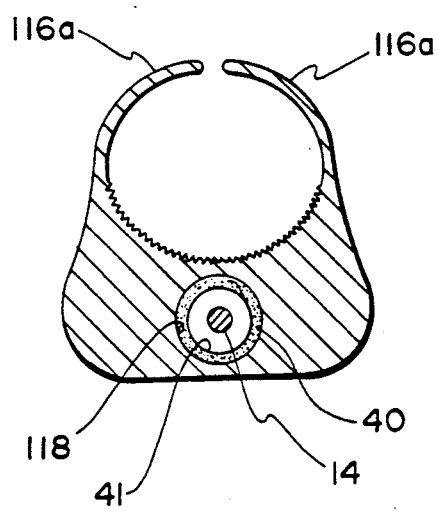
FIG. 7 is a cross sectional view taken along line 7—7 of FIG. 5.
Figure 8:
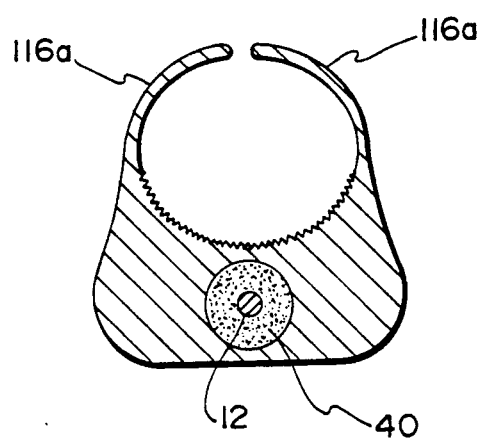
FIG. 8 is a cross sectional view taken along line 8—8 of FIG. 6.

Liner 40 is shown in unhydrated condition in FIG. 5. The tubular liner is securely fixed in chamber 118 and defines passage or bore 41 of substantially larger diameter than the outside diameter of imaging catheter 12. The catheter may therefore be easily inserted into the position shown. The introduction of sterile saline into the annular space about the catheter causes hydration of the liner which swells into the condition depicted in FIG. 6. The expansion of the polymer as it becomes a hydrogel reduces extraneous air pockets within the probe and helps to mechanically fix the catheter in position. In addition, the incorporation of water in the hydrogel mass provides an excellent transmission medium for acoustic energy from the catheter to the exterior of the probe. Water in excess of the hydrogel saturation limit may be directed out of the chamber 118 through ports 119 to the probe-tissue interface. The escape of water helps to maintain an acoustic couple between the exterior of the probe and the insonated tissue, as previously described.

The band 116 of the embodiment of FIGS. 5-8 is located identically to band 16 of the first embodiment but is adjustable to accommodate fingers of different sizes. Such adjustability is achieved by interrupting the band 116 to provide two sections 116a that together arch over a wearer's finger but are capable of flexing slightly upwardly and outwardly to receive fingers of larger girth. It is to be understood that such a two-section band may also be provided for the probe 11 of the first embodiment, if desired.

While in the foregoing, we have disclosed embodiments of the invention in considerable detail for purposes of illustration, it will be understood by those skilled in the art that many of these details may be varied without departing from the spirit and scope of the invention.

We claim:

1. A device for use in intraoperative diagnostic imaging, comprising a probe including an elongated channel-shaped body form of relatively rigid, non-echogenic material substantially transparent to ultrasonic energy and having proximal and distal end portions; said body having an upper surface of concave cross section dimensioned to conform generally with the underside of the portion of a user's finger distal to the second knuckle and having a smooth, rounded lower surface; retaining means provided by said probe for retaining said body in position against the underside of a user's finger; an elongated chamber having an entrance opening in said proximal end portion and extending distally into said body along the longitudinal midline thereof for removably receiving a distal segment of an ultrasound imaging catheter containing an ultrasonic transducer having an imaging plane normal to said longitudinal midline; and mounting means at said proximal end portion of said body for releasably securing the distal segment of such ultrasonic imaging catheter in fully-inserted operative position in said chamber.

2. The device of claim 1 in which said retaining means comprises an integral retention band arching over said body and extending over and engaging the tip portion of a user's finger when said probe is worn.

3. The device of claim 2 in which said band is divided and includes two flexible sections for accommodating fingers of larger girth.

4. The device of claim 1 in which said upper surface of said body is textured to provide a slip-resistant surface.

5. The device of claim 1 in which said elongated chamber terminates in a closed distal end and said distal end portion of said body extends beyond said distal end of said chamber; and Doppler transducer means mounted in said distal end portion of said body for directing, detecting, and transmitting signals representative of blood flow velocity through a vessel contacted by said smooth undersurface of said body at the imaging plane of an ultrasound imaging catheter received in said chamber.

6. The device of claim 5 in which said Doppler transducer means is oriented along a line intersecting the imaging plane of an ultrasound imaging catheter received in said chamber at an angle of approximately 45 degrees.

7. A device for use in intraoperative diagnostic imaging, comprising a probe including an elongated channel-shaped body formed of relatively rigid, non-echogenic material substantially transparent to ultrasonic energy; said body having an upper surface of concave cross section dimensioned to conform generally with the underside of the portion of a user's finger distal to the second knuckle and having a smooth, rounded lower surface; retaining means provided by said probe for retaining said body in position against the underside of a user's finger; an elongated chamber extending distally into said body along the longitudinal midline thereof for removably receiving a distal segment of an ultrasound imaging catheter containing an ultrasonic transducer having an imaging plane normal to said longitudinal midline; and mounting means for releasably securing the distal segment of such ultrasonic imaging catheter in fully-inserted operative position in said chamber; said body having at least one irrigation port extending through said body between said chamber and said lower surface.

8. A device for use in intraoperative diagnostic imaging, comprising a probe including an elongated channel-shaped body formed of relatively rigid, non-echogenic material substantially transparent to ultrasonic energy; said body having an upper surface of concave cross section dimensioned to conform generally with the underside of the portion of a user's finger distal to the second knuckle and having a smooth, rounded lower surface; retaining means provided by said probe for retaining said body in position against the underside of a user's finger; an elongated chamber extending distally into said body along the longitudinal midline therefor for removably receiving a distal segment of an ultrasound imaging catheter containing an ultrasonic transducer having an imaging plane normal to said longitudinal midline; and mounting means for releasably securing the distal segment of such ultrasonic imaging catheter in fully-inserted operative position in said chamber; said body having at least one irrigation port extending through said body between said chamber and said upper surface.

9. The device of claims 7 or 8 in which means are in operative connection with said probe for supplying aqueous irrigation fluid to said chamber.

10. The device of claims 1, 7 or 8 in which a tubular hydrogel liner is disposed within said chamber; said liner having an axial passage for freely receiving the distal end of an imaging catheter when said hydrogel is unhydrated and for firmly engaging said distal end when said hydrogel is hydrated.

11. The device of claim 10 in which means are in operative connection with said probe for supplying irrigation fluid to said chamber for hydrating said hydrogel liner.

12. A device for use in intraoperative diagnostic imaging, comprising a probe including an elongated channel-shaped body formed of relatively rigid, non-echogenic material substantially transparent to ultrasonic energy and having proximal and distal end portions; said body having an upper surface of concave cross sectional contour dimensioned to conform generally with the underside of a user's finger and having a smooth, rounded lower surface; retaining means provided by said probe for retaining said body in position against the underside of a user's finger; an elongated chamber having an entrance opening in said proximal end portion and extending distally into said body along the longitudinal midline thereof; an ultrasound imaging catheter having a distal portion removably received in said chamber; said catheter having an ultrasonic transducer with an imaging plane normal to the axis of aid catheter and said longitudinal midline; and mounting means at said proximal end portion of said body for releasably securing the distal end of said ultrasound imaging catheter in fully-inserted operative position in said chamber.

13. The device of claim 12 in which said retaining means comprises an integral retention band bridging said body and extending over and engaging the tip portion of a user's finger when said probe is worn.

14. The device of claim 13 in which said band is divided and includes two flexible sections for accommodating fingers of larger girth.

15. The device of claim 13 in which said retention band extends along said imaging plane of said catheter.

16. The device of claim 12 in which said upper surface of said body is textured to provide a slip-resistant surface.

17. The device of claim 12 in which said elongated chamber terminates in a closed distal end and said distal end portion of said body extends beyond said distal end of said chamber; and Doppler transducer means mounted in said distal end portion of said body for directing, detecting, and transmitting signals representative of blood flow velocity through a vessel contacted by said smooth undersurface of said body at said imaging plane.

18. The device of claim 17 in which said Doppler transducer means is oriented along a line intersecting said imaging plane at an angle of approximately 45 degrees.

19. A device for use in intraoperative diagnostic imaging, comprising a probe including an elongated channel-shaped body formed of relatively rigid non-echogenic material substantially transparent to ultrasonic energy; said body having an upper surface of concave cross sectional contour dimensioned to conform generally with the underside of a user's finger and having a smooth, rounded lower surface; retaining means provided by said probe for retaining said body in position against the underside of a user's finger; an elongated chamber extending distally into said body along the longitudinal midline thereof; an ultrasound imaging catheter having a distal portion removably received in said chamber; said catheter having an ultrasonic transducer with an imaging plane normal to the axis of said catheter and said longitudinal midline; and mounting means for releasably securing the distal end of said ultrasound imaging catheter in fully-inserted operative position in said chamber; said body having at least one irrigation port extending; through said body between said chamber and said lower surface.

20. The device of claim 19 in which at least one irrigation port extends through said body between said chamber and said upper surface.

21. The device of claims 19 or 20 in which means are in operative connection with said probe for supplying aqueous irrigation fluid to said chamber.

22. The device of claims 12, 19, or 20 in which a tubular hydrogel liner is disposed within said chamber; said liner having an axial passage freely receiving said distal portion of said imaging catheter when said hydrogel is unhydrated and for firmly engaging and supporting said distal portion when said hydrogel is hydrated.

23. The device of claim 22 in which means are in operative connection with said probe for supplying irrigation fluid to said chamber for hydrating said hydrogel liner.

24. A device for use in intraoperative diagnostic imaging, comprising a probe including an elongated channel-shaped body formed of relatively, non-echogenic material substantially transparent to ultrasonic energy and having proximal and distal end portions; said body having an upper surface of concave cross sectional contour dimensioned to conform generally with the underside of a user's finger and having a smooth, rounded lower surface; retaining means provided by said probe for retaining said body in position against the underside of a user's finger; an elongated chamber having an entrance opening in said proximal end portion and extending distally into said body along the longitudinal midline thereof; and an ultrasound imaging catheter having a distal portion received in said chamber and having an ultrasonic transducer with an imaging plane normal to the axis of said catheter.

* * * * *